United States Patent [19]

Robbins et al.

[11] Patent Number: 4,626,429
[45] Date of Patent: Dec. 2, 1986

[54] CONDITIONING OF HAIR WITH AMIDES OF TRIALKYLACETIC ACIDS

[75] Inventors: Clarence R. Robbins, Piscataway; Robert J. Steltenkamp, Somerset, both of N.J.

[73] Assignee: Colgate-Palmolive Company, New York, N.Y.

[21] Appl. No.: 740,697

[22] Filed: Jun. 3, 1985

[51] Int. Cl.$^4$ .................... A61K 7/06; A61K 7/09; A61K 7/11
[52] U.S. Cl. .......................................... 424/70; 8/405; 132/7; 424/47; 424/71; 424/72; 514/483
[58] Field of Search .................... 424/70; 514/483; 260/404, 404.5 PA, 404.5; 132/7

[56] References Cited

U.S. PATENT DOCUMENTS

| | | | |
|---|---|---|---|
| 2,248,089 | 7/1941 | Katzman | 260/404.5 |
| 3,864,368 | 2/1975 | Hartle | 260/404.5 PA |
| 4,332,738 | 6/1982 | Benitez et al. | 260/404.5 PA |
| 4,537,762 | 8/1985 | Fogel et al. | 424/70 |
| 4,548,810 | 10/1985 | Zofchak | 424/70 |

Primary Examiner—Dale R. Ore
Attorney, Agent, or Firm—Herbert S. Sylvester; Murray M. Grill; Norman Blumenkopf

[57] ABSTRACT

Hair is conditioned by applying to it a hair conditioning amide (a mononeoalkanoamide) of trialkylacetic acid (neoalkanoic acid), such as a monoamide of a mono-N-higher alk(en)yl amine and a trialkylacetic acid of 5 to 16 carbon atoms, or a polyamide of a trialkylacetic acid and a polyamine wherein the trialkylacetic acid moieties are of 1 to 10 carbon atoms in each of the alkyls thereof and each of the polyamine moieties contains from 2 to 5 amino groups. The hair conditioning trialkylacetamide is preferably applied to previously wet hair in aqueous solution, emulsion, dispersion or suspension, which is combed into the hair, after which the hair is rinsed with water, leaving on it a conditioning amount of the trialkylacetamide, which improves the condition of the hair by decreasing flyaway, increasing ease of wet combing, increasing ease of dry combing and/or increasing hair luster (especially compared to such luster when quaternary ammonium halide conditioning agents are used repeatedly). Although the conditioning agents of this invention are effective for the treatment of hair, deposit on the hair from aqueous media and are effective to condition the hair, they are removable from it by conventional shampooing, and therefore do not accumulate on the hair, as do quaternary ammonium salt conditioning agents, which accumulation is considered to be objectionable. Also, the present trialkylacetamides do not react with anionic detergent (as do quaternary ammonium halide conditioners), and therefore do not produce objectionable fatty deposits on the hair.

18 Claims, No Drawings

CONDITIONING OF HAIR WITH AMIDES OF TRIALKYLACETIC ACIDS

This invention relates to conditioning of human hair. More particularly, it relates to processes for effecting such conditioning of hair on the head, in which processes a hair conditioning amide of trialkylacetic acid (or neoalkanoic acid), such as a monoamide of a trialkylacetic acid and a mono-N-higher alk(en)yl amine, or a polyamide of a trialkylacetic acid and a polyamine, is applied to the hair, preferably as a rinse, which is an aqueous solution, emulsion, dispersion or suspension, so that a conditioning amount of the trialkylacetamide is left on the hair.

Conditioning rinses for application to human hair have been utilized for many years. Years ago brilliantine was employed to make hair glossy and subsequently other oily preparations and lanolin have been included in hair dressings and rinses to condition hair. More recently, quaternary ammonium salts, which have substantive and antistatic properties, have been utilized in rinses to improve the condition of hair, which is often unmanageable, difficult to comb and sometimes lacking in luster after having been shampooed, as with a synthetic organic detergent (often of the anionic type).

Although quaternary ammonium halides and other quaternary ammonium salts have largely supplanted oily materials as conditioning agents in hair rinses, such "quats" do have certain disadvantages which stimulated research efforts directed to finding better conditioning agents. Quaternary ammonium salts, being cationic, are reactive with anionic materials, such as anionic detergents, and the reaction products tend to be greasy, and form objectionable deposits on the hair. Also, quats tend to build up on the hair with repeated applications, which is objectionable, and such built-up quat deposits, when reacted with anionic detergent, as during shampooing, can form a greasy coating on the hair, which may look dirty. Because the quaternary ammonium salts react with anionic emulsifiers too, the formulating of emulsions of such quats is limited. Due to the mentioned disadvantages research programs have been created, directed to discovering materials which can replace quats in hair conditioning compositions, especially hair conditioning rinses.

It has now been found that amides of trialkylacetic acid (neoalkanoic acid) and mono alk(en)yl amines or polyamines have hair conditioning properties which often are equal to or better than those of quaternary ammonium salts, such as quaternary ammonium halides, and do not possess undesirable characteristics of such quats. The mentioned amides of trialkylacetic acid are described in U.S. patent applications Ser. Nos. 716,871 and 734,508, filed on March 27, 1985 and May 16, 1985, respectively, by Robert J. Steltenkamp and Michael A. Camara, as coinventors, the disclosures of which applications are hereby incorporated herein by reference. In Ser. Nos. 716,871 and 734,508, there are disclosed as new compounds, useful for incorporation in detergent compositions to soften laundry, monoamides of trialkylacetic acid (or neoalkanoic acid) and polyamides thereof, respectively. Although other amides have been incorporated in hair rinses, the amides in the rinses of the present inventions, which are those employed in the present processes, often condition the hair better than do such other amides, and even equal or surpass quaternary ammonium halides in such hair conditioning properties, such as decreasing static or flyaway hair characteristics, improving ease of wet and dry combing of the hair and increasing hair luster and the feeling and appearance of cleanliness In accordance with the present invention a process for conditioning hair comprises applying a hair conditioning amount of an amide of trialkylacetic acid to such hair. In such process the amide, a trialkylacetamide, is preferably applied to the hair by contacting the hair with a solution, suspension, dispersion or emulsion containing 0.1 to 5% by weight of the trialkylacetamide, and such application is while the hair is wet, and preferably is immediately after shampooing of the hair. In such process the trialkylacetamide is preferably a monoamide of a trialkylacetic acid of 5 to 16 carbon atoms and a mono-N-higher alk(en)yl amine, or is a polyamide of such a trialkylacetic acid and a polyamine wherein the trialkylacetic acid moieties are of 1 to 10 carbon atoms in each of the alkyls thereof and in which each of the polyamine moieties contains from 2 to 5 amino groups. Also within the invention, in addition to the described processes, are compositions, such as conditioning hair rinses, which condition human hair by decreasing flyaway, improving ease of wet combing, improving ease of dry combing and/or increasing luster of the hair after shampooing thereof, which comprise an aqueous solution, emulsion, suspension or dispersion of a minor proportion, such as 0.1 to 5%, of a hair conditioning amide of trialkylacetic acid. Preferably, such rinses include a cocoalkyl neodecanoamide and/or a tallowalkyl neodecanoamide in an aqueous alcoholic or aqueous medium but other liquid preparations, such as emulsions, suspensions and dispersions may also be employed providing that they are acceptably stable on storage or so that the amide is readily dispersible before use.

It is a feature of the present invention that the hair conditioning amides utilized in the described processes and compositions are water insoluble and are usually in desired oily or plastic, flowable or spreadable state at normal use temperatures, e.g., 10° to 50° C., preferably 20° to 40° C. The amides employed in this invention are adsorbable or otherwise depositable onto and substantive to human hair from aqueous rinse compositions, but also may be otherwise applied to the hair, as a spray, for example, such as an aqueous or non-aqueous spray, which may be aerosol propelled. The attraction of the hair for the present amides appears to be on a molecular basis, rather than mere physical adherence. Preferred amides used in this invention are higher alkyl and alkenyl [or alk(en)yl] neoalkanoamides of neoalkanoic acids (or of trialkylacetic acids), the acid moieties of which have 5 to 16 carbon atoms, and preferably such moieties contain from 7 to 14 carbon atoms. Although some branching of the hydrocarbyls is acceptable under certain circumstances, it is preferable that the alkyl and alkenyl groups be substantially or essentially linear, and more preferably, they will be linear. Among the more preferable of such neoalkanoamides are those wherein the alkyl or alkenyl is higher, of 8 to 20 carbon atoms, often preferably 12 to 18 carbon atoms, such as may be derived from coconut oil, tallow or hydrogenated tallow or other oil or fat. The mentioned higher alkyls are herein referred to as cocoalkyl, tallowalkyl and hydrogenated tallowalkyl, respectively. It should be noted that in this usage "alkyl" may be inclusive of hydrocarbyl groups containing minor unsaturation, as in tallow alkyl, which contains a minor proportion of a monounsaturated $C_{17}H_{33}$ alkene. However, to avoid any misinterpretation usually reference herein will be to alk(en)yl, which includes both saturated and unsaturated hydrocarbyl.

Neodecanoic acid, which is available commercially from Exxon Chemical Americas in prime and technical grades, is synthesized by reacting a branched nonene and carbon monoxide under high pressure at an elevated temperature in the presence of an aqueous acidic catalyst (Koch reaction). The general mechanism involved includes generation of a carbonium ion followed by complexation with carbon monoxide and the catalyst to form a "complex", which is subsequently hydrolyzed to generate the free acid. The formula of the free acid is:

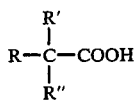

wherein the number of carbon atoms in $R+R'+R''$ is 8; about 31% of the neodecanoic acid is of a structure wherein $R'$ and $R''$ are both methyl and $R$ is hexyl; about 67% is of a structure wherein $R'$ is methyl, $R''$ is of a carbon atoms content greater than that of methyl and less than that of $R$, and $R$ is of a carbon atoms content less than that of hexyl and greater than that of $R''$; and about 2% is of a formula wherein $R'$ and $R''$ are both of carbon atoms content greater than that of methyl and less than that of $R$, and $R$ is of a carbon atoms content less than that of hexyl and greater than those of $R'$ and $R''$. The dissociation constant (Ka) of neodecanoic acid is $4.20 \times 10^{-6}$. Among other neoalkanoic acids that are available may be mentioned others in the 5 to 16 carbon atom content range, such as neopentanoic, neoheptanoic, neononanoic, neodecanoic, neododecanoic, neotridecanoic and neotetradecanoic acids.

To make the neoalkanoamides used in the practice of this invention the neoalkanoic acid, such as neodecanoic acid, may be reacted directly with a higher alkyl- or alkenyl amine [alk(en)yl amine] which is very preferably a linear primary amine, $R'''NH_2$, but also may include slightly branched alkyls having less than 10 or 20% of their carbon atoms contents in branch(es), e.g., as in 2-methyl heptadecyl. The higher alkylamines and alkenylamines employed will normally be of a number of carbon atoms in the range of 8 to 20, often preferably 12 to 18, but may include compounds of more or fewer carbon atoms too, providing that the amides made possess the desired properties, as described herein. Among the more preferred of the amine starting materials are cocoalkyl amine, tallowalkyl amine (which contains a minor portion of oleyl amine), and hydrogenated tallowalkyl amine. Such materials are available from vegetable and animal sources, and amides made from them have been found to be excellent hair conditioning agents, which are compatible with anionic detergents. Also notable as useful amine starting materials are oleyl amine and octyl amine.

The invented amides, which are of the formula:

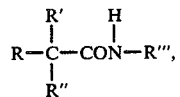

may be made by reacting a neoalkanoyl chloride with a higher alkyl or alkenyl amine, $R'''NH_2$, but a less costly synthesis is directly from the neoalkanoic acid by reacting it with such amine at an elevated temperature. The melting points of the products will normally be low, so that the products will desirably be liquids at room temperature or at normal use temperatures. The melting points of the cocoalkyl-, tallowalkyl- and hydrogenated tallowalkyl neodecanoamides are $<0°$ C., $15°–17°$ C. and $45°$ to $49°$ C., respectively while those of the octyl, oleyl, palmityl and stearyl counterparts are $<0°$ C., $5°$ to $6°$ C., $37°$ to $38°$ C. and $35°$ to $40°$ C., respectively. The refractive indices for the cocoalkyl and octyl neodecanoamides are 1.4626 and 1.4596, respectively. Melting points for the other neoalkanoamides of 5 to 16 carbon atoms in the neoalkanoic acid will be in the $<0°$ to $50°$ C. range and preferably the amides will be oily liquids or plastic or flowable materials at temperatures of $40°$ C. or less.

Although the described N-higher alkyl neodecanoamides are the preferred embodiments of the present invention, other highly branched acids may also be employed for the manufacture of higher alkyl amide antistats. When neopentanoic acid is employed

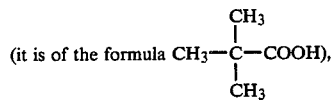

for the manufacture of N-higher alkyl neopentanoamides, useful hair conditioning action is obtainable but not to the extent realized for the higher alk(en)yl neodecanoamides. Normally the neoacid employed to make the hair conditioning monoamides will be of 5 to 16, preferably 7 to 14 carbon atoms, and such acids are obtainable by the described process when highly branched $C_4$–$C_{15}$ or $C_6$–$C_{13}$ olefins are employed as starting materials in the Koch reaction.

In addition to the previously described monoamides of neoalkanoic acids, also found by the present inventors to be useful in hair conditioning processes and compositions are polyamides of trialkylacetic acid(s) and polyamine(s), such as those wherein the trialkylacetic acid moieties are of 1 to 10 carbon atoms in each of the alkyls ($R$, $R'$ and $R''$) and the polyamine moieties contain from 2 to 5 amino groups. Preferred polyamides are those wherein the sum of the carbon atoms of the alkyls of each of the trialkylacetic acid moieties is from 3 to 12 and the polyamine moiety is a diamine or triamine moiety with an alkylene group of 2 to 10 carbon atoms and/or polyoxyalkylene group(s) connecting the amide groups of the polyamide. In such compounds the oxyalkylene of the polyoxyalkylene groups is of 2 to 4 carbon atoms, the number of such oxyalkylene groups in each polyoxyalkylene group is from 1 to 40, and the alkylene group of the polyoxyalkylene alkylene is of 1 to 10 carbon atoms.

In this description the various polyamides, component groups, moieties, and substituents thereof, and reactants will often be referred to in the singular, as will be components of the hair conditioning preparations, such as rinses, but it should be understood that mixtures thereof are also intended. When reference is made to "neoalkyl" or trialkylmethyl, that is intended to describe the "residue" of a neoalkanoic acid after removal of the carboxyl therefrom.

As was previously mentioned, the polyamines are preferably diamines or triamines. The triamines that may be used to make the polyamides that are employable according to the present invention are preferably alkylene polyoxyalkylene triamines, such as those sold by Texaco Chemical Company under the trademark Jeffamine ®. Of such materials Jeffamine T-403, which is of the formula

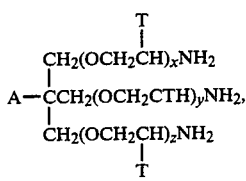

wherein A=ethyl, T=methyl, and x+y+z=5.3, is preferred. The diamines have both amino groups thereof connected by an alkylene polyoxyalkylene moiety or by lower alkylene groups. Of the commercially available diamines containing oxyalkylene groups the Jeffamines are preferred, and the formula of such compounds is

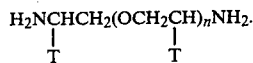

In that formula, while T may often be hydrogen or lower alkyl for the Jeffamines it is methyl and n is in the range of 2 to 10, more preferably 2 to 7. Among such compounds which may be employed are: Jeffamine D-230, wherein n averages about 2.6; Jeffamine D-400, wherein n averages about 5.6; and Jeffamine D-2,000, wherein n averages about 33.1. Of these diamines the most preferred is Jeffamine D-230. Among the non-alkoxylated diamines that are useful are alkylene diamines of 2 to 6 carbon atoms, such as ethylene diamine and hexamethylene diamine.

Instead of using neoalkanoic acids for the manufacture of the present monoamides and polyamides, the corresponding acyl halides may be employed. Such materials are normally used as acid chlorides, such as neodecanoyl chloride, which is available from the Lucidol Division of Pennwalt Corporation, and is described in their product bulletin entitled *Acid Chlorides,* printed in September, 1982, which also generally describes reactions of acid chlorides with amines.

The polyamides which are useful to condition human hair are of the formulas:

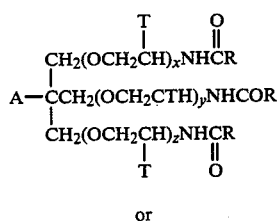

or

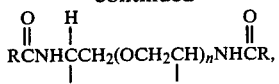

wherein A is alkyl of 1 to 20 carbon atoms or hydrogen, T is methyl or hydrogen, R is a neoalkyl of 4 to 13 carbon atoms, n is from 1 to 40, and x, y and z are each numerals from 1 to 8, and total from 4 to 10. Such compounds may be made by reacting a neoalkanoyl chloride with a suitable polyamine but, as with the monoamides, a less costly synthesis is directly from the appropriate neoalkanoic acid by reacting it with such polyamine. The melting points of the described polyamides, like those of the previously described monoamides, will normally be low, so that the products will desirably be liquids, preferably viscous, oily liquids. Such physical state is unusual for primary and secondary amides of comparable or even lower molecular weight because of strong intermolecular forces that are characteristic of the amide functionality. However, the viscous oily liquid state of the materials of the present invention is considered to be highly desirable because it is considered to improve adherence to the hair (which "adherence" may really be the result of molecular attraction) and contributes to conditioning actions. It is also important for the polyamides of this invention to be essentially water insoluble, while yet being readily distributable throughout an aqueous medium at normal use temperatures of a hair rinse, such as in the 10° to 50° C., range often preferably 20° to 45° C. Thus, when choosing polyamine and neoalkanoic acid reactants, selecting such reactants with desired proportions of hydrophilic and hydrophobic groups, such as ethylene oxide and propylene oxide (or butylene oxide) allows one to control the hydrophile-lipophile balance of the polyamide to be made, and thereby to "fine tune" its water insolubility so that it can be a more effective hair conditioner in the intended process or product.

It is considered that the best hair conditioners of the polyamides are those made from a neoalkanoic acid, such as neodecanoic acid, and a polyoxypropylene triamine, such as Jeffamine T-403. Other Jeffamines, such as Jeffamines D-230, D-400 and D-2,000, may also be employed to make the invented polyamides, and of these Jeffamine D-230 is best, apparently because the other Jeffamines result in products which are less effective as hair conditioning agents because of their higher contents of oxypropylene groups, higher molecular weights and deficiency of hydrophilic characteristics, which contribute to lowering the adsorption thereof onto the hair. When the polyamine is ethylene diamine or hexamethylene diamine hair conditioning activities like those of the other of the polyamides are obtainable but the ethylene and hexamethylene diamides are not considered to be as effective hair conditioners as the polyamides made with the described trialkylacetic acid(s) and Jeffamine T-403 or Jeffamine D-230.

The Jeffamine polyamines that may be employed to manufacture the antistatic polyamides of this invention are described in a booklet entitled JEFFAMINE Polyoxypropyleneamines, published by Texaco Chemical Company and copyrighted in 1978 by Jefferson Chemical Company, Inc. Formulas of such polyamines are given at pages 2 and 3 thereof and typical physical properties for them are listed at pages 3 and 4. Uses of the Jeffamines are described throughout the booklet, primary among which is that of a component of synthetic resins, such as epoxy resins and polyurethanes. In a bibliography near the end of the booklet, at pages 61–64, textile applications of the Jeffamines and related materials are listed and summarized, but no references are to uses for conditioning human hair. Also, none of the references, as mentioned in the Jeffamine booklet, describes or suggests a polyamide of the type described herein, and the desirable characteristics thereof.

Triamides that are useful in the processes and preparations of this invention are of the formula

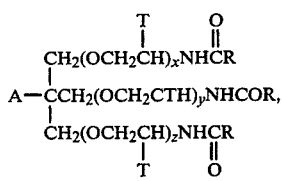

wherein A is alkyl of 1 to 20 carbon atoms or hydrogen, T is methyl or hydrogen, R is a neoalkyl of 4 to 13 carbon atoms, and x, y and z are each numerals from 1 to 8, and total 4 to 10. More preferably, A is an alkyl of 1 to 4 carbon atoms, T is methyl, R is a neoalkyl of 4 to 9 carbon atoms, and x, y and z are each numerals from 1 to 3, which total from 4 to 8. Still more preferably, A is an alkyl of 1 to 3 carbon atoms, T is methyl, R is neoalkyl of 4 or 9 carbon atoms and x, y and z are each numerals from 1 to 3, which on the average total from 4.5 to 6. Most preferably, A is ethyl, T is methyl, R is neoalkyl of 9 or about 9 carbon atoms and x, y and z are each numerals from 1 to 3, the total of which averages about 5.3. The preferred diamides of this invention are of the formula

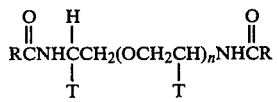

wherein T is methyl or hydrogen, R is a neoalkyl of 4 to 13 carbon atoms, and n is from 1 to 40. More preferably, T is methyl, R is neoalkyl of 4 to 9 carbon atoms and n is a numeral from 2 to 10. Still more preferably, T is methyl, R is neoalkyl of 4, 6 or 9 carbon atoms, and n is a numeral from 2 to 7. Most preferably, T is methyl, R is a neoalkyl of 9 or about 9 carbon atoms and n is an average of about 5.6. Other useful diamides are those of a neoalkanoic acid of 5 to 10 carbon atoms with an alkylene diamine of 2 to 6 carbon atoms. Among such compounds those preferred are N,N'-ethylene-bis-neodecanoamide and N,N'-hexamethylene-bis-neodecanoamide.

It will be seen from the above formulas and descriptions of components and substituents thereof that the amine radicals of the monoamines and polyamines (including diamines) are completely converted to amide form. However, while such amides are highly preferred, it is contemplated that incompletely "amidified" polyamines which are at least ⅔ amidified may also be employed as hair conditioners. They will have some of the undesirable properties of quaternary ammonium salts, in that they may be reactive with anionic detergents, but it is considered that such reaction and any resulting undesirable effects thereof will often be tolerable because only a minor proportion of the reactive amine radicals will not have been converted to non-reactive amides. Also any adverse effects due to the presence of unreacted amine groups may be ameliorated by blending with other completely amidified hair conditioners of this invention.

Mixtures of the polyamides may be employed in any desired and effective proportions. Thus, for example, N,N'-ethylene-bis-neodecanoamide may be mixed with N,N'-hexamethylene-bis-neodecanoamide; N,N'-ethylene-bis-neodecanoamide may be mixed with N,N'-hexa-methylene-bis-neopentanoamide; the tri-neodecanoamide of Jeffamine T-403 may be mixed with the di-neodecanoamide of Jeffamine D-230; and the tri-neodecanoamide of Jeffamine T-403 may be mixed with N,N'-ethylene-bis-neo-decanoamide, to mention only a few of the possible combinations. Also, 3- and 4-member and other combinations of the polyamide may be made. Additionally, such mixtures or components thereof may be mixed with monoamides, such as tallow-alkyl neodecanoamide, and mixtures of the monoamides, such as 1:1 mixtures of cocoalkyl- and tallowalkyl neodecanoamides, may also be made and are successful hair conditioning agents, as in aqueous rinses.

Although the amides utilized in this invention are essentially non-reactive with anionic materials, such as synthetic organic anionic detergents, dispersants, suspending agents and emulsifiers, and can be incorporated in shampoos and rinse preparations, which may contain such anionic materials, they may also be employed as solutions, in which such anionic compounds may or may not be present. Also, in addition to aqueous and alcoholic media, including aqueous alcoholic media, in which the conditioning amides may be dissolved, they may be applied to the hair in various non-aqueous media, such as those based on lower alkanols, e.g., ethanol, lower glycols, e.g., propylene glycol, and polyols, e.g., glycerol. In some embodiments of the invention the conditioning amide may be applied to the hair directly, without the use of any other liquid medium, and in some cases it may be sprayed or foamed onto the hair, preferably as an aqueous spray or foam or an "aerosol" spray or foam from a pressurized container or from a liquefied gas. In all instances it is preferred that the application of the conditioning amide be to wet hair, as directly after shampooing, but it may be applied to dry or damp hair too, although the conditioning results may not be as good. After application, the amide should be combed (or brushed) into the hair.

When the conditioning amide or mixture thereof is to be applied to the hair it will most preferably be from an aqueous rinse. Such rinse may be of any suitable viscosity, even as low as one centipoise (at 20° C.) but usually will be within the range of 500 to 5,000 centipoises, preferably 1,000 to 4,000 centipoises. The viscosity of the hair conditioning composition, which is preferably a thickened emulsion, aqueous dispersion or aqueous alcoholic (aqueous ethanolic or a water-glycol-alcohol solution) rinse, can be adjusted by the employment of suitable thickeners, such as lauric myristic diethanolamide, sodium carboxymethyl cellulose, polyvinyl alcohol or polyacrylamide, or other suitable non-interfering gum or polymeric thickener, when such adjustment is considered to be desirable.

Although 100% monoamide or polyamide hair conditioner may be applied to the hair and combed into the hair to condition it in accordance with the present invention, normally the concentration of the conditioning amide in the liquid medium from which it is applied, such as an aqueous medium, will be less than 20% and in aqueous, alcoholic and aqueous alcoholic rinses it will be in the range of 0.1 to 5%, preferably 0.3 to 2%, and most preferably 0.5 to 1.5%. Preferred rinse compositions, either solutions, emulsions, dispersions, or suspensions, are generally aqueous and sometimes may desirably be aqueous alcoholic. In such primarily aqueous media the water content will usually be in the range of 50 to 99%, preferably 80 to 98% and more preferably 90 to 97%. For aqueous alcoholic media the alcohol (ethanol) content will usually be from 10 to 90%, preferably 60 to 80% and more preferably about 70%, and the water content will be from 10 to 90%, preferably 20 to 40% and more preferably about 30%.

The hair conditioning amides of the present invention are satisfactorily substantive to human hair and are adsorbed on the surfaces thereof when applied to the hair from liquid media, such as aqueous media. Although substantive, not all the conditioning amide will be deposited and held to the hair during normal rinse application. It will normally be desirable to have from about 0.01 to 1.5% by weight of the conditioning amide available for application to the hair, based on the weight of the hair to which it is to be applied. Preferably such ratio will be in the range of 0.02 to 0.8% and more preferably 0.1 to 0.5%. The weight of rinse employed, based on the weight of hair treated will normally be from 1% to 150%, preferably 2 to 80% and more preferably 10 to 50%.

The temperature at which the hair is treated and conditioned with the present amides will usually be within the range of 10° to 50° C., preferably 20° to 45° C., and more preferably 25° to 45° C., e.g., about 40° C. Such will be the temperatures of the water (usually rinse water to remove shampoo) employed to wet the hair before application of the hair conditioning agent and of the rinse water (to remove the hair conditioning rinse). Such waters will normally be city water and will preferably be of relatively low hardness, such as 0 to 100 p.p.m., as calcium carbonate, although waters of hardnesses as high as 250 p.p.m. may also be used. Additionally, it will be desirable that the total salt content of the water be less than 500 p.p.m. and preferably it will be less than 200 p.p.m.

Normally the hair conditioning amides employed in the processes of this invention will be applied to "living" hair on the human head immediately after shampooing and rinsing of the hair. At such stage, the hair, cleaned of dirt and oil, tends to become "raspy" and hard to comb in both wet and dry condition. It also tends to accumulate electrostatic charges, making it difficult to manage and causing the characteristic "flyaway" appearance. Frequently, although the hair is clean, it has lost some of its sheen or luster in shampooing. By treating the hair with the conditioning amides of the present processes a "coating" of such amide(s) is held to the hair, which lubricates the hair and makes combing easier, both in wet and dry states. Such coating of substantive amide also improves the hair luster and decreases "flyaway" tendencies, making the hair more manageable and easier to comb or set in desired shape.

In addition to improving the characteristics of the hair, the present conditioning agents also are compatible with most cleaning agents employed in shampoos. Thus, they do not adversely react with anionic detergents and thereby do not interfere with the cleaning of the hair by shampoos based on such detergents. They do not form undesirable insoluble products by reaction with such detergents. Thus, the invented processes and compositions are useful for conditioning human hair without undesirable reactions that have accompanied other conditioning agents, such as those based on quaternary ammonium halides. Another significant advantage of the present processes and compositions is that the conditioning amides are easily removable from the hair by conventional shampoos, of both anionic and nonionic types, so objectionable conditioner build-up is easily avoidable. Furthermore, in many instances the present processes and compositions are superior in conditioning powers to those in which the quaternary ammonium halides are employed or are present.

The following examples illustrate but do not limit the invention. Unless otherwise indicated, all parts are by weight and all temperatures are in °C.

EXAMPLE 1

Monoamides and multiamides (or polyamides) of decanoic acid were dissolved in suitable aqueous alcoholic media for dissolving the respective amides and were tested for conditioning effects. The amides tested were cocoalkyl neodecanoamide, tallowalkyl neodecanoamide, the diamide of Jeffamine D-400

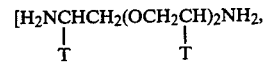

wherein T is methyl and n is 5.6]

and neodecanoic acid, and the triamide of Jeffamine T-403

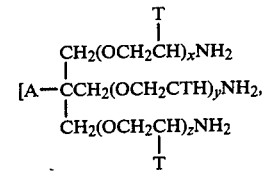

wherein A = ethyl, T = methyl and x + y + z = 5.3]

and neodecanoic acid. The amides are made by reaction of approximately stoichiometric quantities of neodecanoic acid or neodecanoyl chloride with the appropriate amine, as previously described in this specification. The various conditioning solutions (rinses) made include: (a) 1 gram of cocoalkyl neodecanoamide, 66 grams of ethanol and 33 grams of water; (b) 1 gram of tallowalkyl neodecanoamide, 82 grams of ethanol and 17 grams of water; (c) 1 gram of J-DEC (diamide condensation product of Jeffamine D-400 and neodecanoic acid), 50 grams of ethanol and 49 grams of water; and (d) 1 gram of TRI-DEC (triamide condensation product of Jeffamine T-403 and neodecanoic acid), 60 grams of ethanol and 39 grams of water. Also made for comparative purposes was a solution of 1 gram of SAC (stearalkonium chloride), 29 grams of ethanol and 70 grams of water. In all cases the water employed was deionized and the solutions were at room temperature, 23° C.

In the tests, to rate hair conditioning by measuring wet combing, dry combing and flyaway characteristics of the conditioning agents, human hair tresses, each of which weighed three grams, were wet under tap water, which was at 41° C., and different tresses were each treated with 1.75 grams of one of the amide solutions. The solution was rubbed into the tress and was combed through it, using 20 comb strokes, after which the tress was rinsed under 41° C. tap water (of about 100 p.p.m. hardness, as calcium carbonate) for 15 seconds, was combed for another ten strokes, and was set aside for evaluation. A control tress was shampooed with a sodium lauryl sulfate based shampoo and was rinsed, and was also evaluated for conditioning properties. The control tress was the most difficult to comb when wet, with the TRI-DEC and J-DEC solutions being less difficult to wet comb (the J-DEC being easier to comb than the TRI-DEC) and with the SAC being appreciably easier to comb than the J-DEC. The CO-DEC tress was much easier to wet comb than the SAC tress and the T-DEC tress was easiest of all to wet comb.

After the tresses were dried they were combed and the order of ease of combing was established as T-DE>CO-DEC>SAC>J-DEC>TRI-DEC>SLS. The manageability (reverse of flyaway) of the tresses was also observed and it was found that the order of manageability was T-DEC>CO-DEC=J-DEC>S-AC>TRI-DEC>SLS.

No differences in luster were establishable between the SAC and DEC treated tresses after the single treatments but after three treatments, using 0.5% of the rinses containing CO-DEC, T-DEC AND SAC, respectively, with 10% triethanol-ammonium sulfate aqueous shampoos between treatments, the amide-treated tresses were more lustrous, apparently due to undesirable build-up of a reaction product of the SAC and the anionic detergent of the shampoo. Also, shampooing left little of the amide on the hair, whereas the SAC treated tress had not been cleaned as well, and contained the mentioned reaction product.

In a further experiment, utilizing the monoamides and SAC (for comparison), at a concentration of 0.5% in the aqueous alcoholic media described, the CO-DEC and T-DEC tresses were about equal to or better than the SAC tress in ease of wet combing (in single application tests).

The amide-treated tresses of this invention were also noticeably improved, compared to the shampooed control tresses, in other desirable hair conditioning characteristics. They were more manageable (less subject to flyaway), easier to comb when dry, and had better luster (shine or sheen). Compared to the SAC treated tress the amide-treated tresses appeared more lustrous or shinier. Also, when the treatments are repeated twice, with shampooings with a sodium lauryl sulfate shampoo being effected between rinse treatments, the amide treated tresses feel cleaner, apparently because they do not contain a build-up of amide whereas the SAC treated tresses contain a build-up of the reaction product of stearalkonium chloride and the anionic detergent of the shampoo.

EXAMPLE 2

When aqueous alcoholic solutions are made, like those of Example 1 but using 0.2%, 0.5%, 1% and 2% of hydrogenated tallowalkyl neodecanoamide, cocoalkyl neopentanoamide, oleyl neodecanoamide, octyl neodecanoamide, palmityl neodecanoamide and mixed $C_{12-14}$ alkyls neodecanoamide, the solutions (rinses) are satisfactory hair conditioners. Such amides are made in the manner described in the preceding specification, and are dissolved to the extent possible in 70:30 or 50:50 ethanol-water solvent medium. Hair tresses like those described in Example 1, but with both bleached and unbleached hair being employed in separate tresses for each type of treatment, are treated in the manner described in Example 1, with the various solutions mentioned, and are evaluated for conditioning effects imparted to them by such solutions. All the mentioned amides condition the hair, although the neopentanoamides are less effective than the neodecanoamides, and the neoheptanoamides are intermediate in effects. Also, those conditioning rinses containing higher percentages of the amides condition better. While all the amides condition the hair, and all are better than the control shampoo with respect to wet combing, dry combing and manageability after treatment, they are also better than SAC in luster and clean feel after repeated treatments and intermediate shampooings with triethanolammonium lauryl sulfate (TEALS) shampoos. The invented neoalkanoamides have significant advantages over conditioning agents and rinses based on quaternary ammonium salts when repeated treatments are used, in luster and clean feeling properties, even when they may not be superior to quat rinses in wet combing, dry combing or manageability characteristics.

EXAMPLE 3

When the experiments of Example 1 are repeated but with other polyamides employed instead of those described in Example 1, similar conditioning results are obtainable. The replacing amides include neodecanoamides of Jeffamine D-230, Jeffamine D-2,000, ethylenediamine and hexamethylenediamine, and the neoheptanoamides of Jeffamine T-403, Jeffamine D-230, Jeffamine D-400 and Jeffamine D-2,000. Such polyamides are employed at a concentration of 0.5% in 70:30 ethanol:deionized water solvent media, and the treatments of hair effected are those described in Example 1, with the treated hair tresses being both bleached and unbleached, so as to simulate actual usage of conditioning hair rinses. All the solutions and all the treatments are effective in conditioning the hair to improve the ease of wet and dry combings, decrease flyaway and increase luster, compared to the control (same as in Example 1). Also, all the amides are readily removable from the hair by normal shampooing, thereby avoiding objectionable build-up on the hair which tends to make it appear greasy and not as clean as desired.

EXAMPLE 4

The experiments of Examples 1-3 are repeated, using aqueous dispersions in warm water (about 40° C.) of the various amides described. Conditioning effects of the types described in the foregoing examples are also obtainable. However, it is preferred to utilize 0.3% or 0.5% of the amides in the water, and to use sufficient rinse to deposit a conditioning amount (about 0.5 to 1% of the hair weight) on the hair tress, so as to decrease deposition of any droplets or particles of amide on the hair and so as to promote molecular, rather than macrodeposition.

EXAMPLE 5

A mixture of equal parts of cocoalkyl neodecanoamide and tallowalkyl neodecanoamide is made and dissolved in a 70:30 alcohol:water solvent medium to produce a rinse solution containing 0.6% of the total of the hair conditioning amides, and hair tresses are treated with it in the manner described in Example 1. The results obtained are like those of Example 1, with the tresses treated with the mixture of amides being better than stearalkonium chloride and better than the SLS control in ease of wet combing, ease of dry combing and manageability (less flyaway). Also, after repeated treatments with the conditioning agents and shampooing with TEALS shampoo the treated hair tresses are more lustrous than the SAC rinse treated hair. Additionally, it is confirmed that the neodecanoamides are readily removable by conventional shampooing whereas the SAC is not (apparently because it forms an adherent and insoluble reaction product with the detergent).

EXAMPLE 6

When, instead of applying the various alkanoamides of the previous examples to the hair in aqueous or aqueous alcoholic or other solvent or suspending medium they are applied directly to the hair as liquids (for those that are in the liquid state at room temperature or at the temperature of application) conditioning effects are obtainable. Such application may be by a pressurized spray, as from an atomizer, or may be from an aerosol composition, such as is made by dissolving the amide in aerosol propellant, such as a 50:50 mixture of Propellants 11 and 12 or other suitable aerosol propellant. It may also be as a foam, from a pressurized dispenser. In such an application 1 part of tallowalkyl neodecanoamide is dissolved in the propellant mixture and is sprayed onto the hair, with about 25 parts of ethanol or aqueous ethanol (to prevent loss of the amide by excessive misting), or it is dispensed onto the hair as a foam. The amide is then combed through the hair and the hair is rinsed, as in Example 1. The treated tresses are satisfactorily conditioned and are superior to a control and to SAC treated hair in the various conditioning characteristics mentioned in Example 1.

EXAMPLE 7

When the experiments of Examples 1-6 are repeated, varying the contents of the various components of the rinses and other preparations ±10, ±20 and ±30%, while maintaining them within the ranges of proportions and percentages mentioned in the specification, and also when others of the described amides are employed in hair preparations other than hair rinses, such as gels, sprays, mousses, foams, combs (for dispensing conditioning agent) or in shampoos, permanent waving and hair dyeing preparations, useful conditioning effects will also be obtained, compared to controls, and luster and apparent cleanliness will be significantly improved, compared to when similar preparations based on stearalkonium chloride hair conditioning agent or other quaternary ammonium halides, such as distearyldimethyl ammonium chloride, cetyltrimethyl ammonium bromide or laurylmyristyldimethyl ammonium chloride, are employed.

The invention has been described with respect to various illustrations and examples thereof but is not to be limited to these because it is evident that one of skill in the art with the present specification before him will be able to utilize substitutes and equivalents without departing from the invention.

What is claimed is:

1. A process for conditioning hair which comprises applying a hair conditioning amount of an amide of trialkylacetic acid to such hair, which amide is selected from the group consisting of monoamides of trialkylacetic acid of 5 to 16 carbon atoms and mono-N-higher alk(en)yl amine, polyamides of trialkylacetic acid and polyamine, and mixtures thereof, wherein the alkyls of the trialkylacetic acid moieties are of 1 to 10 carbon atoms each, and in which each of the polyamine moieties contains from 2 to 5 amino groups.

2. A process according to claim 1 wherein the trialkylacetamide is appled by contacting the hair with it after shampooing.

3. A process according to claim 2 wherein the trialkylacetamide is applied to the hair as a rinse composition comprising 0.1 to 5% by weight of such trialkylacetamide, 10 to 90% of water and 10 to 90% of alcohol.

4. A process according to claim 1 wherein the hair is wet before application thereto of the amide of trialkylacetic acid, the trialkylacetamide is applied to the hair, the trialkylacetamide is combed into the hair, and the hair is rinsed with water, whereby there is left on the hair a conditioning amount of the trialkylacetamide, which improves at least one of the following: (a) decrease in flyaway tendency; (b) ease of wet combing; (c) ease of dry combing; and (d) luster, and which is readily removable from the hair by shampooing.

5. A process according to claim 1 wherein the trialkylacetamide is applied in aqueous solution, the N-higher alk(en)yl of the monoamide is of 8 to 20 carbon atoms, and the sums of the numbers of carbon atoms of the alkyls of each of the trialkylacetic acid moieties of the polyamides are from 3 to 12, and the polyamine moiety thereof is a diamine or triamine moiety with alkylene group(s) of 2 to 10 carbon atoms and/or polyoxyalkylene alkylene groups connecting the amide groups of the polyamide, with the oxyalkylene of the polyoxyalkylene groups being of 2 to 4 carbon atoms, with the number of such groups in each polyoxyalkylene group being from 1 to 40 and with the alkylene groups of the polyoxyalkylene alkylene being of 1 to 10 carbon atoms.

6. A process according to claim 5 wherein the higher alk(en)yl of the monoamide is linear and of an average of 12 to 18 carbon atoms and the polyamide is of the formula

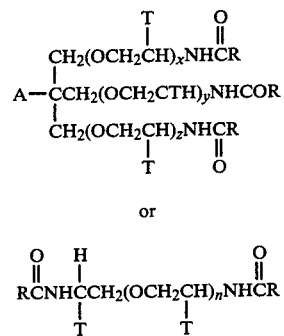

or $$\overset{O}{\overset{\|}{R}}\overset{H}{\underset{|}{N}}\overset{}{C}CH_2(OCH_2CH)_n\overset{O}{\overset{\|}{N}HCR}$$
$$\overset{|}{T}\phantom{CH_2(OCH_2CH)_n}\overset{|}{T}$$

wherein A is alkyl of 1 to 20 carbon atoms or hydrogen, T is methyl or hydrogen, R is a trialkylmethyl of 4 to 13 carbon atoms, n is from 1 to 40, and x, y and z are each numerals from 1 to 8, and total from 4 to 10.

7. A process according to claim 6 wherein the trialkylacetamide is a monoamide of mono-N-higher alk(en)yl amine of an average of 12 to 18 carbon atoms and trialkylacetic acid of 5 to 10 carbon atoms.

8. A process according to claim 7 wherein the monoamide is of a mono-N-higher alkyl amine wherein the higher alkyl is of an average of 12 to 18 carbon atoms, and of a trialkylacetic acid of ten carbon atoms (neodecanoic acid).

9. A process according to claim 8 wherein the monoamide is cocoalkyl neodecanoamide.

10. A process according to claim 8 wherein the monoamide is tallowalkyl neodecanoamide.

11. A process according to claim 8 wherein the hair is wet before application thereto of the amide of trialkylacetic acid, the trialkylacetamide is applied to the hair, the trialkylacetamide is combed into the hair, and the hair is rinsed with water, whereby there is left on the hair a conditioning amount of the trialkylacetamide, which improves at least one of the following: (a) decrease in flyaway tendency; (b) ease of wet combing; (c) ease of dry combing; and (d) luster, and which is readily removable from the hair by shampooing.

12. A process according to claim 6 wherein the trialkylacetamide is of the formula

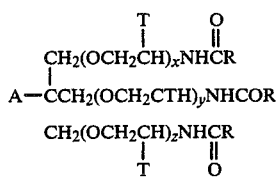

wherein A is an alkyl of 1 to 4 carbon atoms, T is methyl, R is a neoalkyl (trialkylmethyl) of about 4 to 9 carbon atoms, and x, y and z are numerals from 1 to 3, which total from 4 to 8.

13. A process according to claim 12 wherein, in the formula of the polyamide, A is ethyl, R is neoalkyl (trialkylmethyl) of about 9 carbon atoms, T is methyl, and x, y and z are each numerals from 1 to 3, which total an average of about 5.3.

14. A conditioning hair rinse composition which conditions human hair by decreasing flyaway, improving ease of wet combing, improving ease of dry combing and/or increasing luster of the hair after shampooing thereof, which comprises a solution of 0.1 to 5% of an amide of trialkylacetic acid, 10 to 90% of water and 10 to 90% of alcohol, which trialkylacetamide is selected from the group consisting of monoamides of trialkylacetic acid of 5 to 16 carbon atoms and mono-N-higher alk(en)yl amine, polyamides of trialkylacetic acid and polyamine, and mixtures thereof, wherein the alkyls of the trialkylacetic acid moieties are of 1 to 10 carbon atoms each, and in which each of the polyamine moieties contains from 2 to 5 amino groups.

15. A rinse composition according to claim 14 wherein the trialkylacetamide is cocoalkyl neodecanoamide.

16. A rinse composition according to claim 14 wherein the trialkylacetamide is tallowalkyl neodecanoamide.

17. A rinse composition according to claim 16 which is a solution of 0.3 to 2% of tallowalkyl neodecanoamide in an aqueous alcoholic medium which comprises 60 to 80% of ethanol and 20 to 40% of water.

18. A rinse composition according to claim 15 which is a solution of 0.3 to 2% of cocoalkyl neodecanoamide in an aqueous alcoholic medium which comprises 60 to 80% of ethanol and 20 to 40% of water.

* * * * *